United States Patent [19]

Taylor et al.

[11] Patent Number: 4,876,278

[45] Date of Patent: Oct. 24, 1989

[54] ZINC GLYCEROLATE COMPLEX AND ADDITIONS FOR PHARMACEUTICAL APPLICATIONS

[75] Inventors: Reginald M. Taylor, Hawthorn; Alan J. Brock, North Adelaide, both of Australia

[73] Assignee: Glyzinc Pharmaceuticals Limited, Perth, Australia

[21] Appl. No.: 278,338

[22] Filed: Dec. 1, 1988

Related U.S. Application Data

[63] Continuation of Ser. No. 56,483, Apr. 23, 1987, abandoned.

[51] Int. Cl.$^4$ .............................. A61K 31/315; 514 844; 514 494
[52] U.S. Cl. ..................................................... 514/494
[58] Field of Search ................................ 514/844, 494

*Primary Examiner*—Stanley J. Friedman
*Attorney, Agent, or Firm*—Cushman, Darby & Cushman

[57] ABSTRACT

The method of applying to a human or animal body a curative or control medium which is a zinc glycerolate complex (Glyzinc) formed as a reaction product of zinc oxide, or a zinc oxide forming material, and glycerol produced at a temperature of from 120° C. to 300° C. in which the zinc glycerolate complex is deposited subcutaneously in the human or animal body either directly or through transdermal absorption.

4 Claims, No Drawings

ZINC GLYCEROLATE COMPLEX AND ADDITIONS FOR PHARMACEUTICAL APPLICATIONS

This is a continuation of application Ser. No. 056,483, filed Apr. 23, 1987, now abandoned.

This invention relates to the use of Glycerato Zinc (II) ($C_3H_6O_3Zn$), also called zinc glycerolate, and hereinafter sometimes referred to as "Glyzinc", previously known as a prophylactic or therapeutic agent for internal and external inflammatory conditions, and referred to and claimed in United Kingdom Letters Patent No. 2101132B, Taylor, R.M. and Brock, A.J. entitled "Zinc glycerolate compound as a pharmaceutical compound" based on Australian Patent Application No. PE 6602 dated Nov. 24, 1980, and the corresponding U.S. Pat. No. 4,544,761.

In the earlier referred to patent, the zinc glycerolate was basically designed for application to the skin to prevent sunburn or to treat external skin conditions, taking into account the platey morphology of the compound and was specifically directed to such products as ultraviolet protective skin creams because of the extensive cover afforded by the platelets, and shaving creams because of the high lubricity, and while it was known that the compound was suitable for surface application in this way, its use for subcutaneous and intramuscular application or as a nutrient trace element and as an effective antimicrobial or antibacterial agent was not known.

The present invention is therefore additional to the said Letters Patents and embraces the use of this compound in an extended field for curative or control purposes in humans or animals, including its application as an antimicrobial or antibacterial medium.

The invention is not limited to the use of the compound as denoted by the stoichiometric formula given above but is extended to include the chemical derivatives of this compound where another element or elements may partially replace the zinc values contained therein by substitution or by modifications of the Glyzinc as for example by the partial or complete pyrolysis. Therefore this invention relates also to the supplying of trace elements other than zinc by the use of these derivatives where such trace element deficiencies may exist in humans or animals.

The technique of the invention for the abovementioned applications have now been found not to be limited by the method of use described in the earlier Patent, and this invention extends such methods to oral ingestion, administration subcutaneously or intramuscularly, together with additives, such as copper ions, and extends also the method of applications to such other means that may ensure effective absorption whether applied externally or internally.

The method of this invention consists in applying to a human or animal body a zinc glycerolate complex (Glyzinc) formed as a reaction product of zinc oxide, or a zinc oxide forming material, and glycerol produced at a temperature of from 120° C. to 300° C. to form hexagonal plate-like crystals having a substantially greater development in two dimensions in one plane than in a third dimension normal to the other plane, characterised by subcutaneously depositing the zinc glycerolate complex.

Treatment can be effected by dermal application and for instance rubbing to cause subcantaneous deposition of the complex which hydrolyses and releases zinc and glycerol.

The method however includes direct deposition of the zinc glycerolate complex such as by parenteral application.

The invention comprises a zinc glycerolate complex (Glyzinc) which is a reaction product of zinc oxide or a zinc oxide forming material and glycerol at a temperature of from 120° C. to 300° C. to form hexagonal plate-like crystals having a substantially greater development in two dimensions than in a third dimension normal to the other two dimensions, when applied subcutaneously to the human or animal body.

The complex can have additives and can be applied using fluid carriers.

It will be seen that the present invention extends the use of Glyzinc as a slow-release formulation of zinc, either when applied to the skin and rubbed in or applied by a roll-on device or when administered parenterally (intramuscularly or subcutaneously) as a suspension in isotonic salt (e.g. sodium chloride) or sugar solution.

Glyzinc and related or derived zinc oxides have also been found to be effective as anti-inflammatory agents when administered in the above fashion, and Glyzinc and related or derived zinc oxides, when administered orally, as gastro-protective agents have been found to minimise gastric ulceration and aid the healing of gastric ulcers.

It is also now found that Glyzinc as a percutaneous carrier for transitional metal ions (e.g. copper, manganese, iron) which have therapeutic value and for such necessary trace elements where a deficiency in their concentration levels is to be overcome or where an increase in their concentrations in the animal or human body is desirable.

Glyzinc can be described as a white, lustrous powder which may exhibit quite variable crystalline particle sizes and morphologies depending on the method of formation. The powder is readily hydrolysed in water but is stable in the dry state and may be readily rubbed into the skin after application either as a dry powder or as a dispersion in various compatable vehicles e.g. dimethylsulphoxide, isopropanol, glycerol or mixtures thereof.

The larger sized crystallite particles exhibiting a pronounced hexagonal morphology endow the compound with a high lubricity which is an advantageous attribute for topical dermal application. The lubricity of this general type of product appears to be due to the physical and chemical properties of the product as prepared by one of the preferred methods described by Radoslovich, E.W., Raupach, M., Slade, P. G. and Taylor, R. M. (1970). (Crystalline cobalt, zinc, iron and manganese alkoxide of glycerol. Aust. J. Chem. 23; 1963-1971) or as such as that of Hambly, T. J. and Snow, M. R. (1983), (The crystal and molecular structure of zinc monoglycerolate. Aust. J. Chem. 36; 1249-1253).

Finely milled zinc oxide preparations will mimic Glyzinc as a means for delivering zinc percutaneously but they are technically difficult to prepare, are more difficult to rub into the skin and have a less satisfactory shelf life than Glyzinc due to their tendency to reaggregate in the dry state or deteriorate with moisture. The preferred means for delivering zinc transdermally for therapeutic purposes is therefore as Glyzinc in the dry state or as a vehicle suspended powder.

Zinc is an essential nutrient trace element that is necessary for cell division and cell repair for example in the case of wounds and burns (human skin is considered to contain about 20% of all the body zinc). This element is also necessary for a large number of other bodily functions for example the metabolism of proteins and carbohydrates, and during rapid growth and during puberty especially in the adolescent male.

Deficiency in the body levels and availability of zinc can manifest itself in a variety of diseases and body malfunctions, see Hoffer, A. and Walker, W. (1978) (Orthomolecular Nutrition. Keats Publishing Co. Connecticut.)

Zinc is inefficiently absorbed by the human gastrointestinal tract especially when zinc-binding complexing agents are also ingested with foodstuffs e.g. phytic acid present in many cereal products.

Attempts have been made to devise the alternative delivery systems for zinc to ensure adequate zinc repletion in zinc-deficient states. For example, one such modern parenteral formulation requires intramuscular injection of a zinc salt emulsified into an oil, the zinc being released as the oil (a triglyceride of plant origin is degraded in vivo, see Brewer, G. J. (1982)(Molecular mechanisms of zinc action in Inflammatory Diseases and Copper.) (ED J. R. Sorenson) Humana Press, New Jersey, p529). This procedure is cumbersome, it may be painful and there is little control over the actual rate of zinc release which can vary widely between different individuals.

Glyzinc on the other hand when applied to the skin in the dry state (e.g. from a roll-on dispenser, which activates the tissue for better absorption, or as an aerosol) or as a suspension in certain non-aqueous media, provides an adequate means of ensuring zinc availability by means of transdermal absorption. Evidence that this is so has been obtained from experiments with partly shaved rats, showing that radioactivity is present in several internal organs (especially those organs which bind zinc after parenteral administration) following the dermal application of $^{65}$Zn-Glyzinc. Further evidence has been obtained in other experiments which have shown that Glyzinc applied at appropriate times to the skin of partly shaved rats will largely reduce the development of an experimentally induced arthritis, which is also beneficially treated by the subcutaneous injection of Glyzinc or certain zinc salts.

The oral applications of zinc salts e.g. zinc sulphate has been shown to facilitate the healing of human gastric ulcers, see Frommer, D. J. (1975) (The healing of gastric Ulcers by zinc sulphate. Med. J. Aust. 2; 793–796.) and to prevent stomach injury by gastrotoxins as referred to by Esplugues, J. V. and Bulbena, O., Escolar, G., Marti-Bonmatic, E., and Esplugues, J. (1985) (Effects of zinc acexamate on gastric mucosal resistance factors. European J. Pharmacol. 109;145-151).

However a notable disadvantage of zinc sulphate and other water-soluble zinc salts is their highly bitter and metallic taste. Even zinc oxide powders have this umpleasant taste. By contrast Glyzinc is quite acceptable to the palate either in the dry state or as freshly suspended (but not aged) dispersions in neutral pH aqueous media. Direct evidence that Glyzinc administered orally as an aqueous dispersion is gastro-protective has been obtained from short-term experiments with fasted, stressed rats subjected to gastrotoxins such as 12% alcohol or asprin (50 mg per kg body weight) which invariably cause rapid and severe haemorrhagic lesions in the gastric mucosa of these animals. Glyzinc at doses of 25 mg per kg significantly reduces the rat gastric lesions index without causing the gastric irritation, evidenced by an increase in gastric volume, that is manifest by similar doses of zinc salts e.g. zinc sulphate.

The following examples show details of tests on rats which lead to the conclusion that Zinc Monoglycerolate ZMG, (Glyzinc) which is a lubrous powder that readily rubs into the skin, slowly-hydrolyses releasing zinc and glycerol and causes minimal irritation when injected.

EXAMPLE 1

The Glyzinc compound was suspended in a mixture of 4 vols dimethylsulphoxide (DMSO) with 1 vol. glycerol. These slurries were applied once daily to the shaved backs (ca.16 cm$^2$) of male hooded rats with established arthritis. This polyarthritis was initiated 12 days previously by injecting 50 µl of an adjuvant containing 1% killed Mycobact tuberculosis in squalene, into the tailbase. On days 12, 16, and 19 after this, the arthritis severity was determined by measurng body weight, rearpaw thickness, tail thickness and assigning an arthritic score to the front paws. Treatments were given on days 12 to 15 inclusive: no treatment; the vehicle =DMSO-Glycerol only; Glyzinc in vehicle; 10% Cu(II)—Glyzinc in vehicle.

The results indicated that the vehicle along supressed the arthritis to some degree and minimised weight loss but it was clear that Glyzinc was remarkably effective. This was not a spurious result due to nondiseased rats, since there was a significant 'rebound' in the arthritis after ceasing treatment.

The copper (II)—containing Glyzinc was much less active and caused more weight loss than Glyzinc alone.

EXAMPLE 2

Glyzinc was applied to male hooded rats with preestablished arthritis on day 12 et seq. It was formulated in 4 rub-on liquids, namely:
(a) DMSO with glycerol (4:1, $^v$/v)
(b) Isopropanol (=rubbing alcohol) with glycerol (4:1, $^v$/v)
(c) Methyl Salicylate (=oil of wintergreen)
(d) Squalene (a hydrocarbon present in human sebum).

These were applied to groups of 3 rats with 4 untreated controls. The dose applied was 62.5 mg/kg Glyzinc in 2.5 ml/kg vehicle once daily for 4 days, rubbed into shaved dorsum. This followed generally the system of Example 1.

The results of these tests were:
(i) Confirmation of previous finding in Example 1 that the Glyzinc with DMSO and glycerol is a potent anti-inflammatory agent;
(ii) Glyzinc with isopropanol and glycerol was rather less effective;
(iii) Glyzinc with squalene, a natural skin lipid, was ineffective (no glycerol was present in this formulation).

Other findings were:
(a) Methyl salicylate is too toxic, used undiluted as a vehicle. (All rats were dead after 2nd dose).
(b) The significant rebound in arthritis signs after cessation of treatment (days 16–19).

In further examples Glyzinc was applied therapeutically as a rub on powder on the shaved skin of Hooded rats with developing adjuvant arthritis on days 12-15 postadjuvant. Glyzinc (100 mg/kg/day) suppressed arthritis measured on day 16 (p<0.01). Talc (250 mg/kg/day) did not (p>0.35).

The efficacy of the dermal application of Glyzinc may be demonstrated by a comparison of front and rearpaw swellings following various treatments.

In this particular experiment on established adjuvant induced arthritis, 11 rats were untreated, talc was applied in 8 rats, Glyzinc was used in 12 animals, and 4 received subcutaneous Glyzinc. At the start of treatment of these four groups, there was no significant difference in absolute rearpaw thickness on analysis on variance with an overall mean value of 6.32 mm ($\pm 0.51$ standard deviation). There was also no significant difference amongst groups in frontpaw arthritis scores, or in body weight.

After treatment for 4 days, the measured absolute thickness of rearpaws differed (anova p<0.02) amongst the four groups. The relative extent of swelling during treatment was calculated from the difference in thickness during these four days; the extent of swelling differed very significantly (p<0.01) amongst the groups, as shown in the following data.

Comparison of rearway swelling (mm) during treatment.

|  | Untreated | Talc dermal | Glyzinc dermal | Glyzinc subcutaneous |
| --- | --- | --- | --- | --- |
| Paws Swelling | 22 | 16 | 24 | 8 |
| mean | 1.57 | 1.67 | 0.62 | 0.34 |
| s.d. | 0.51 | 0.87 | 0.57 | 0.69 |

The animals treated with Glyzinc showed a mean of 0.6 mm swelling during treatment, which was significantly less (by t-test p<0.01) than the 1.6 mm swelling in the other rats. There was a corresponding difference in front-paw arthritis scores as shown in table 2. Front-paw scores increased to a lesser extent in the Glyzinc treated than the other animals (p<0.01).

Comparison of frontpaw score changes during treatment.

|  | Untreated | Talc dermal | Glyzinc dermal | Glyzinc subcutaneous |
| --- | --- | --- | --- | --- |
| Score change |  |  |  |  |
| mean | 2.9 | 1.5 | 0.7 | 0.5 |
| s.d. | 1.1 | 0.9 | 1.3 | 1.4 |

The rats lost 5.9 g body weight during treatment on average, and with a standard deviation of 10.1g no significant difference was found amongst the groups; weight loss tended to be least in the group treated with dermal glyzinc (mean 3.1 g).

Percentage inhibition was estimated by comparing the rearpaw swelling during treatment with that in controls 59$\pm$12% inhibition of rearpaw swelling occurred on applying 100mg/kg/day Glyzinc dermally. 78$\pm$17% inhibition of swelling occured with 63 mg/kg glyzinc given subcutaneously.

Glyzinc was also effective applied dermally in DMSO glycerol (4:1, $v$/v) or injected s.c. in saline at 60 mg/kg/day. After ceasing treatment there was a marked rebound in tail and paw swelling.

Applied propylactically in 7 doses subcutaneously on alternate days Glyzinc (60 mg/kg s.c.) was as effective as Aurothiomalate (ATM, 12 mg/kg) in preventing arthritis development in Dark Agouti rats and prevented arthritis in hooded rats which do not respond to ATM.

The following table illustrates the relative prophylactic efficiency of glyzinc injected subcutaneously with that of saline and two reference drugs against polyarthritis induced in Dark Agouti rats by avidine.

| Treatment (s.c. alt. days 0 ... 16) | DIFFERENCE (day 0 to day 21) | | |
| --- | --- | --- | --- |
|  | REARPAW mm | FRONTPAW score | WEIGHT g |
| Saline | 2.73 | 3.7 | $-32$ |
| Glyzinc (63 mg/kg) | 0.03 | 0.0 | $-7$ |
| Aurothiomalate (13 mg/kg) | 2.15 | 5.0 | $-20$ |

Equivalent doses of peroral/subcutaneous zinc salts (sulphate, acetate, glycinate) did not prevent/treat this rat polyarthritis but caused severe tissue irritation. Given subcutaneously $^{65}$Zn was readily transferred from dermally applied $^{65}$Zn-Glzinc to faeces.

Returning again to the use of Glyzinc, tests have demonstrated that Glyzinc may be used to treat medical disorders in humans involving zinc insufficiency (due to malabsorption, inadequate diet, parasitism etc.) by dermal application of the dry powder or dispersions of this powder in various vehicles for skin application; particularly when applied by an activating device such as a roll-on dispenser which gives a smooth and even distribution while massaging the tissue to make it more active to increase absorption. Also dosage can readily be controlled by the number of passes of the applicator, which also acts to ensure an even and well mixed compound where additives such as copper are dispensed with the Glyzinc.

It has been found that Glyzinc is suitable for subcutaneous or intramuscular administration to provide a slow-release depot of zinc that is far less irritant to the site of application than equivalent applications of zinc oxide or zinc salts. Tests have shown that Glyzinc is extremely non-irritant when injected subdermally compared with other forms, e.g. zinc sulphate.

It has also been shown that Glyzinc applied dermally, subcutaneously or intramuscularly is a beneficial agent to treat pre-established inflammation or to prevent or minimise the onset of inflammatory symptoms, particularly those associated with arthritis, psoriasis and other conditions of long-standing duration.

During research it was found also that Glyzinc is a beneficial adjunct for the pretreatment of gastric bleeding/ulceration and is superior to the use of conventional antacids which are based on, for example, the oxides of calcium, magnesium and aluminium, and for the prophylactic use to protect the gastric mucosa from stresses or toxin-induced injury.

Assessments of Glyzinc were carried out in Examples 3, 4 and 5 as follows:

EXAMPLE 3

Tests of antimicrobial activity of Glyzinc showed that this substance was inhibitory and microbiocidal when tested under laboratory conditions against Candida albicans ATCC 10231 and Staphylococcus aureus NCTC 4163.

The tests were undertaken to determine if Glyzinc was active against a wide range of clinical isolates of bacteria and yeasts; to determine the minimum inhibitory concentration of this substance for bacteria and to assess its ability to kill a selected range of bacteria.

The test methods used were based on the principles laid down by the National Committee for Clinical Laboratory Standards (1983), Methods for dilution antimicrobial susceptibility tests for bacteria that grow aerobically; Tentative Standard M7-T and in Gradwohl's Clinical Laboratory Methods and Diagnosis 1970, Vol. 2 page 1407, ed. Frankel, S., Reitman, S. and Sonnenwirth, Bacterial Sensitivity Testing. Methods had to be modified to permit testing of the insoluble powder.

The culture media used was:
Nutrient Broth No. 2 (Oxoid) NB
Tryptone Soya Agar (Oxoid) TSA
Inactivating diluent where appropriate: Nutrient broth No. 2 with 3% Tween 80.
Temperature for cultivation of organisms: $35° C. + -1° C.$
Incubation time: 18-24 hrs.
Cultures: Laboratory isolates of various bacteria.

The qualitative tests of antibacterial activity of Glyzinc compared to zinc oxide were carried out as follows:

Agar plates containing 10 mg/ml Glyzinc and 20 mg/ml zinc oxide were inoculated with $10^5$–$10^6$ log phase bacterial growths comprising a strain of each of the following, Pseudomonas aeruginosa, Escherichia coli, Proteus mirabilis, Staphylococcus aureus, Streptococcus faecalis and Candida albicans.

The results confirmed that all organisms grew on the TSA plates containing 20 mg/ml zinc oxide. All growths were inhibited by 10 mg/ml Glyzinc.

To test the quantitation of inhibitory activity of Glyzinc against several strains of each test organism, serial dilutions of Glyzinc in TSA to give final concentrations of 10, 5, 2.5, 1.25, 1.0, 0.5 and 0.25 mg per ml were prepared.

Using a replicator $10^5$–$10^6$ organisms from broth cultures in log phase growth were inoculated onto the plates which were incubated for 18 hours.

The results are set out as follows:

| Organism | No. of Strains Tested | Minimum inhibitory concentration (mg/ml) |
|---|---|---|
| Ps. aeruginosa | 6 | 2.5 |
| E. coli | 7 | 1.0 |
| P. mirabilis | 7 | 2.5 |
| S. aureus | 7 | 0.5 |
| Str. faecalis | 1 | 2.5 |
| Candida albicans | 3 | 2.5 |

From this the conclusion is that all organisms were inhibited by a concentration of 2.5 mg/ml Glyzinc. Staph. aureus and E. coli seemed to be more susceptible than the other organisms tested. No significant variation in susceptibility between strains of the same genera was noted.

To test the bactericidal activity of Glyzinc, concentrations of 5 mg/ml and 25 mg/ml were prepared in nutrient broth. These represent 10 times the MIC for sensitive and more resistant bacteria. Tests were run in duplicate by inoculating each concentration with $10^6$–$10^7$ bacteria. S. Aureus, P mirabilis and Ps. aeruginosa were tested.

Tubes were placed at 35° C. in a shaking rack and were sampled at 15 minute intervals for 60 minutes and at 30 minute intervals for a further 60 minutes by withdrawing 1 ml samples and adding these to 10 ml 3% Tween 80 diluent. Diluent broths were sampled by plating 2 ul to TSA plates. This method detects a 99% kill.

The following results were observed:

| | Time to cause a 99% reduction in count with: | |
|---|---|---|
| | 5 mg/ml Glyzinc | 25 mg/ml Glyzinc |
| Ps. aeruginosa | 60 mins | 60 mins |
| P. mirabilis | 120 mins | 60 mins |
| S. aureus | Greater than 120 mins | Greater than 120 mins |

Concentrations of Glyzinc of 5 and 25 mg/ml resulted in a 99% kill of Ps. aeruginosa in 60 minutes. P. mirabilis was more resistant to killing as 5 mg/ml Glyzinc took 120 minutes to kill 99% of these organisms.

S. aureus was incompletely killed by Glyzinc at 25 mg/ml with less than a 99% reduction in count being observed at 120 minutes.

From the above it can be concluded that contact times of approximately 60 minutes are necessary to demonstrate substantial killing of micro-organisms. The test results suggest that gram negative bacteria are more susceptible to killing than staphylococci.

The tests performed on Glyzinc confirm that this substance has a broad antibacterial activity and is capable of preventing the multiplication of the pathogenic bacteria commonly encountered in the laboratory. With sufficiently prolonged contact GZ is also capable of killing bacteria. These characteristics are essential elements in any clinically useful antibacterial agents.

EXAMPLE 4:

The objective was the detection of bacterio-and fungi-static activity of antiseptic powder samples of Glyzinc.

In this example 0.1 gram of powder was spread over the surface of a 47 mm, 0.45 micron cellulose acetate membrane. The membrane was placed on an agar which has been seeded with bacteria or fungal spores. After incubation a clear area of no growth indicated bacterio/fungistatic activity of the powder.

It should be noted that while the membrane seed method was chosen as the most relevant in vitro test case the following limitations apply:
(a) That the antimicrobial compounds are diffusable through the membrane and agar,
(b) That the antimicrobial reagents do not react with the culture medium.

| Test Organisms | NCTC |
|---|---|
| Pseudomonas aeruginosa | 6749 |
| Staphylococcus aureus | 8196 |
| Escherichia coli | 4163 |
| Candida albicans | A.T.C.C. 10231 |
| Mixed Mildew | |
| Aspergillus niger | MRL 72 |
| Aspergillus flavas | MRL 5 |
| Syncephalastrum racmosum | MRL 427 |
| Alternaria radicina | MRL 523 |
| Paecilomyces varioti | MRL 436 |
| Specific Mould Trichophyton rubrum | MDU |

The culture media used was Nutrient Agar (Oxoid CM3) and Minimal Salts Agar.

In this test the size of the clear one was a measure of diffusibility as well as antibacterial fungal activity—the size of the zone must not be construed as a quantitative evaluation of antibacterial fungal activity.

From the tests the following bacteriostatic evaluation was made:

The Glyzinc powder under investigation showed strong bacteriostatic action against S. aureus and E. coli and good bacteriostatic action against Ps. aeruginosa and the yeast C. albicans.

The results further showed that the product under investigation had good diffusability through the medium Nutrient Agar.

The powder under investigation was seen to be fungistatic with the fungi tested, however the sample did not show the diffusibility capabilities as revealed in the bacteriostatic work. This may be attributable to hydroscopic effects as incubation of the plates was in a humid environment to promote mould growth.

The control membrane sample (without the addition of any powders) partially inhibited the growth of the fungi used in the test and only results with almost complete inhibition or greater are attributable to the effect of the powder itself, and it is clear that the powder showed significant bacterio and fungistatic effects against all the organisms tested.

EXAMPLE 5

Quantitative testing for antimicrobial activity was carried out as follows.

The challenge organisms were:
Candida albicans ATCC 10231
Staphylococcus aureus NCTC 4163

Culture media were:
Tryptone Soya Agar (OXOID) (TSA)
Nutrient Broth No. 2 (OXOID) (NB)

The inactivating diluent was Nutrient Broth No. 2 with 2% Lecithin and 3% Tween 80.

Temperature for Cultivation of Organisms: 34° C.
Temperature for Antimicrobial Challenges: 34° C.
Incubation Time (post exposure): 24-36 hours.

The method used an agar diffusion using small circular wells cut from the agar plate and filled with plugs of medium containing known concentrations of Glyzinc, "O" and, as a known antimicrobial control, mercuric oxide. Plates were swab-inoculated with a mid.log culture (about $3 \times 10^7$ viable organisms/ml) of each test organism.

The result was inhibition zones (mm diam.) due to 10 mg. of agent.

| Agent | Candida albicans | Staph aureus |
|---|---|---|
| HgO | 22 | 33 |
| "O" | no zone | no zone |
| Glyzinc | 16 | 16 |

The test showed that compound "O" had no significant activity at concentrations up to about 20 mg/ml (2% w/v) against either of the organisms tested. On the other hand, Glyzinc appeared to have significant antibacterial and antifungal activity. Subsequent tests were performed to quantify these activities.

A minimum inhibitory concentration using agar dilution with minor modifications introduced to accommodate the insolubility of Glyzinc and to allow the widest possible range of inoculum density to be challenged resulted in the following:

A dilution series of Glyzinc in TSA was prepared in quadruplicate: an appropriate amount of the solid was suspended thoroughly in 50 ml molten TSA; half this volume was poured into a petri dish and then replaced with fresh molten medium. This two-fold dilution procedure was repeated until a series of plates covering the range of concentration 20 mg/ml to 0.062 mg/ml was constructed. Duplicate pairs of these plates were inoculated either immediately after the plates were set and dried, or after they had been stored in the refrigerator overnight.

Mid log-phase NB cultures of each organism were applied to each plate with a bacteriological loop, then streaked for single colonies. This method ensured that the widest possible variety of inoculum density was examined.

The result confirmed minimum inhibitory concentrations for Glyzinc as follows:

| Organism | Concentration of Glyzinc in TSA required to prevent growth of single colonies.° |
|---|---|
| Candida albicans | 1.5 mg/ml |
| Staph aureus | 0.15 mg/ml |

In general, dense inocula were inhibited by concentrations of Glyzinc between $2\times$ and $4\times$ higher. Inhibitory concentrations in fresh plates and refrigerated plates were indistinguishable. These results were the means of four determinations.

The conclusion was that compound Glyzinc may be active against Candida at concentrations as low as 0.15% w/v, and against Staph aureus at even lower concentration, viz. 0.015%. This level of activity is not inconsistent with the proposal that Glyzinc might be used as an antiseptic or therapeutic agent on human skin.

To test the activity of Glyzinc at $10 \times$ MIC as a function of time, the following method was used.

Suspensions containing either no Glyzinc, or Glyzinc at 2.5 mg/ml or 15.0 mg/ml were inoculated with the test organisms (separately) to give an initial density of $10^6$ viable cells/ml. Cultures were incubated with sufficient agitation to keep the Glyzinc in suspension, and samples were withdrawn to 10 vol Inactivating Diluent at intervals for up to 2 h. These samples were diluted further as appropriate, then plated to TSA to allow enumeration of surviving organisms.

The result showing a percent kill as a function of time were as follows:

| | | % KILL AT | | |
|---|---|---|---|---|
| Organism | Glyzinc conc. | 15 min. | 45 min. | 90 min. |
| Candida albicans | 15 mg/ml | 66% | 90% | 99.9% |
| Staph aureus | 2.5 mg/ml | 90% | 99.9% | 99.99% |

We claim:

1. A method for the treatment of gastric bleeding or ulceration comprising orally or parenterally administering to a human an effective amount of a zinc glycerolate complex ($C_3H_6O_3Zn$) comprising plate-like crystals.

2. A method for the treatment of gastric bleeding or ulceration comprising orally or parenterally administering to a human an effective amount of a zinc glycerolate complex ($C_3H_6O_3Zn$) formed as a reaction product of zinc oxide, or a zinc oxide forming material, and glycerol and a temperature of from 120° to 300° C. said complex being in the form of hexagonal plate-like crystals having a substantially greater extension in two dimensions in one plane than in a third dimension normal to the other plane.

3. A method for the treatment of gastric ulcers in humans or for the treatment of a zinc deficiency in animals or humans comprising orally or parenterally administering to a human suffering from gastric ulcers or to humans or animals suffering from a zinc deficiency an effective amount of a pharmaceutrical composition comprising in a pharmaceutically acceptable carrier suitable for oral or parenteral administration an effective amount of a zinc glycerolate complex ($C_3H_6O_3Zn$) comprising hexagonal plate-like crystals.

4. A method for the therapeutic or prophylactic, or both, treatment of gastric ulcers and lesions in a human or animal body comprising orally administering to said human or animal an effective amount of a zinc glycerolate complex formed as a reaction product of zinc oxide, or a zinc oxide forming material, and glycerol at a temperature of from 120° C. to 300° C., said complex being in the form of hexagonal plate-like crystals a substantially greater extension in two dimensions in one plane than in a third dimension normal to the other plane.

* * * * *